(12) United States Patent
Gaines, Jr.

(10) Patent No.: US 8,505,137 B1
(45) Date of Patent: Aug. 13, 2013

(54) EQUINE CT TABLE

(75) Inventor: Arthur J. Gaines, Jr., Huntersville, NC (US)

(73) Assignee: Artec Imaging, LLC, Cornelius, NC (US)

(*) Notice: Subject to any disclaimer, the term of this patent is extended or adjusted under 35 U.S.C. 154(b) by 360 days.

(21) Appl. No.: 12/958,391

(22) Filed: Dec. 1, 2010

Related U.S. Application Data

(63) Continuation-in-part of application No. 12/358,186, filed on Jan. 22, 2009, now abandoned.

(60) Provisional application No. 61/265,751, filed on Dec. 1, 2009, provisional application No. 61/011,960, filed on Jan. 22, 2008.

(51) Int. Cl.
*A61B 6/04* (2006.01)
*A47B 13/00* (2006.01)

(52) U.S. Cl.
USPC ....... 5/601; 5/611; 5/83.1; 5/86.1; 5/81.1 RP; 5/81.1 HS; 108/147; 108/94; 269/17; 269/32; 269/56; 269/71; 378/209; 128/845; 600/415; 600/427; 600/407

(58) Field of Classification Search
USPC .................. 108/147, 94; 119/753, 755, 756; 269/17, 32, 56, 71; 378/209; 128/845; 600/415, 427, 407; 5/601, 611, 83.1, 86.1, 5/81.1 RP, 81.1 HS
See application file for complete search history.

(56) References Cited

U.S. PATENT DOCUMENTS

| | | | | |
|---|---|---|---|---|
| 6,094,760 A * | 8/2000 | Nonaka et al. | ................ | 5/601 |
| 6,101,644 A * | 8/2000 | Gagneur et al. | ............ | 5/81.1 R |
| 6,155,970 A * | 12/2000 | Dykes et al. | .................... | 600/22 |
| 6,385,481 B2 * | 5/2002 | Nose et al. | ..................... | 600/415 |
| 6,424,854 B2 * | 7/2002 | Hayashi et al. | ............... | 600/415 |
| 6,457,196 B1 * | 10/2002 | Dykes et al. | ...................... | 5/655 |
| 6,640,364 B1 * | 11/2003 | Josephson et al. | ................ | 5/601 |
| 6,944,492 B1 * | 9/2005 | Persoons et al. | ............. | 600/415 |
| 7,216,383 B2 * | 5/2007 | Heinl et al. | ........................ | 5/601 |
| 7,818,838 B2 * | 10/2010 | Erbel et al. | ........................ | 5/601 |
| 7,874,030 B2 * | 1/2011 | Cho et al. | .......................... | 5/601 |
| 2004/0057557 A1 * | 3/2004 | Nafstadius | .................... | 378/209 |
| 2006/0197530 A1 * | 9/2006 | Damadian et al. | ............ | 324/318 |

* cited by examiner

*Primary Examiner* — Peter M Cuomo
*Assistant Examiner* — Ifeolu Adeboyejo
(74) *Attorney, Agent, or Firm* — Everman Law Firm, PA; Gregory R. Everman

(57) ABSTRACT

An equine CT table for positioning a horse during a CT ("computed tomography") scan. The table is positioned above the patient couch and communicates with the conventional CT system for examination of a horse without requiring mechanical or electrical attachments between the CT system and table. The table includes a frame carrying a tracking system, a linear movement system and a carousel upon which the horse is positioned. Prior to examination, positioning of the horse on the table may be manually adjusted linearly and/or radially in any direction to properly align the horse. Infinitely positionable cantilever members are provided to support horse's appendages. The tracking system identifies movement of the CT couch and mimics the movement with the linear movement system to enter and retract the horse from the gantry at predetermined positioning.

10 Claims, 15 Drawing Sheets

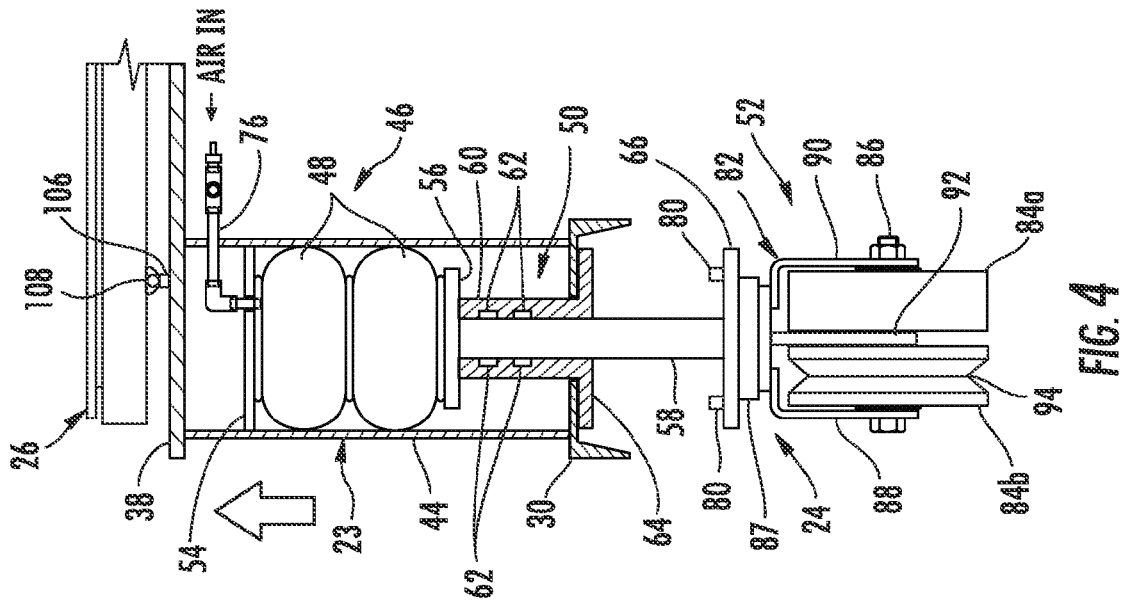
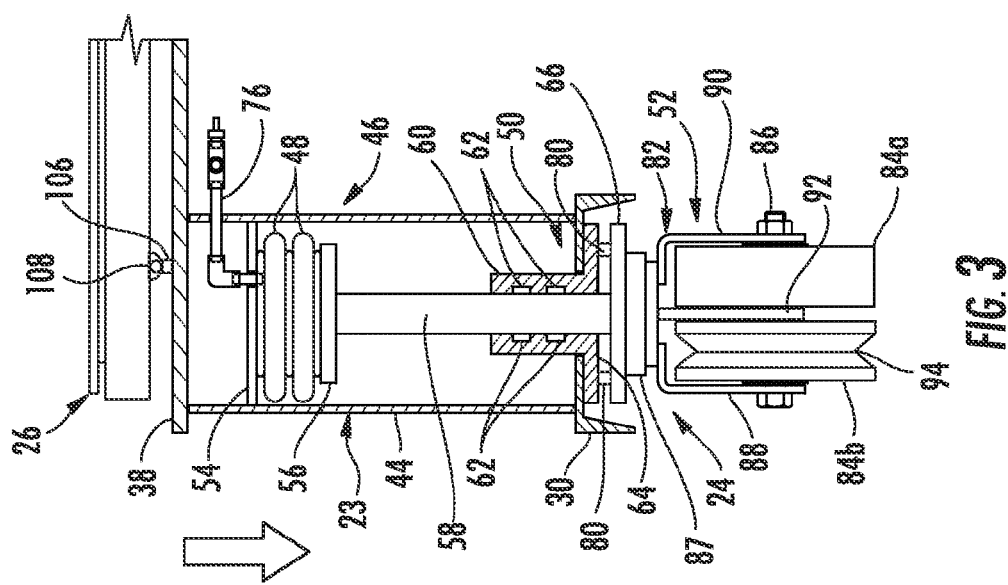

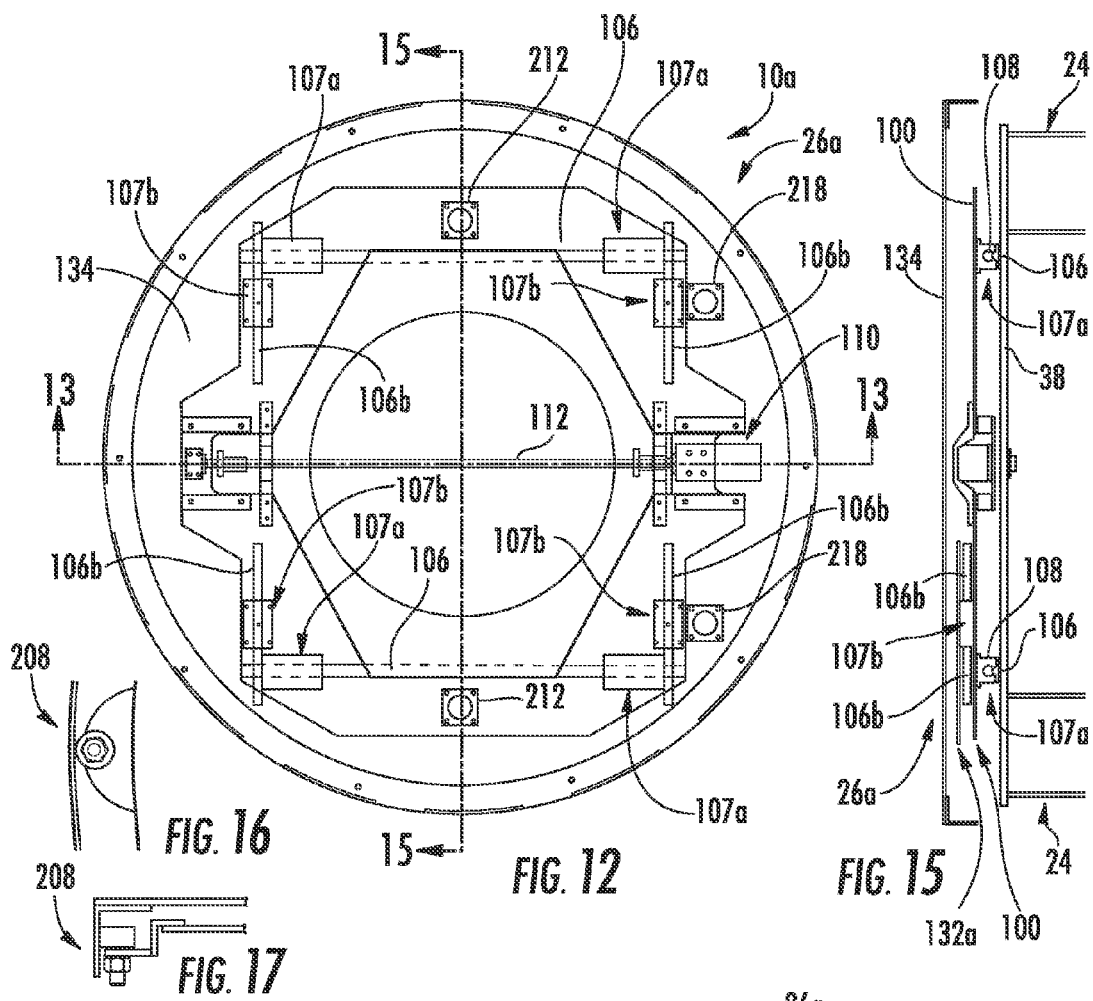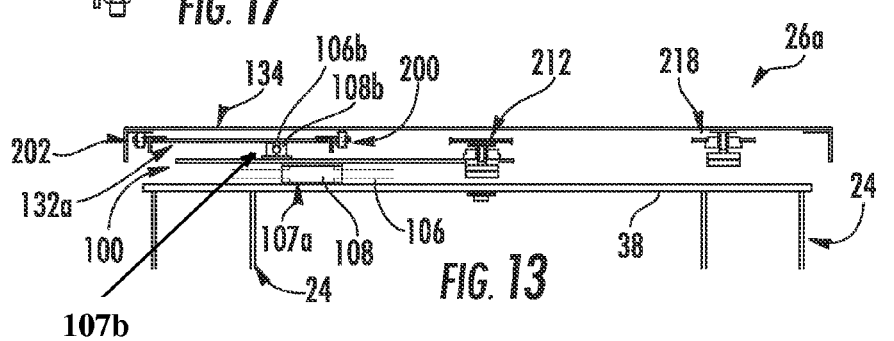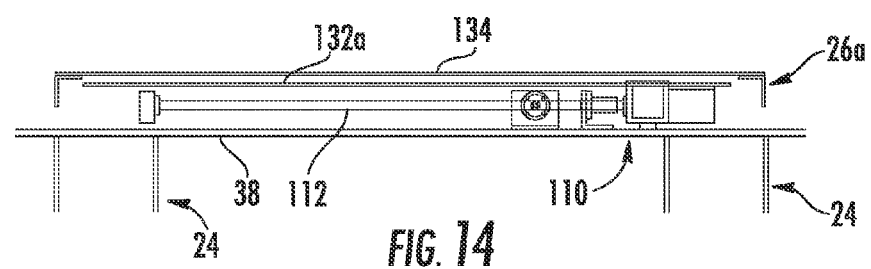

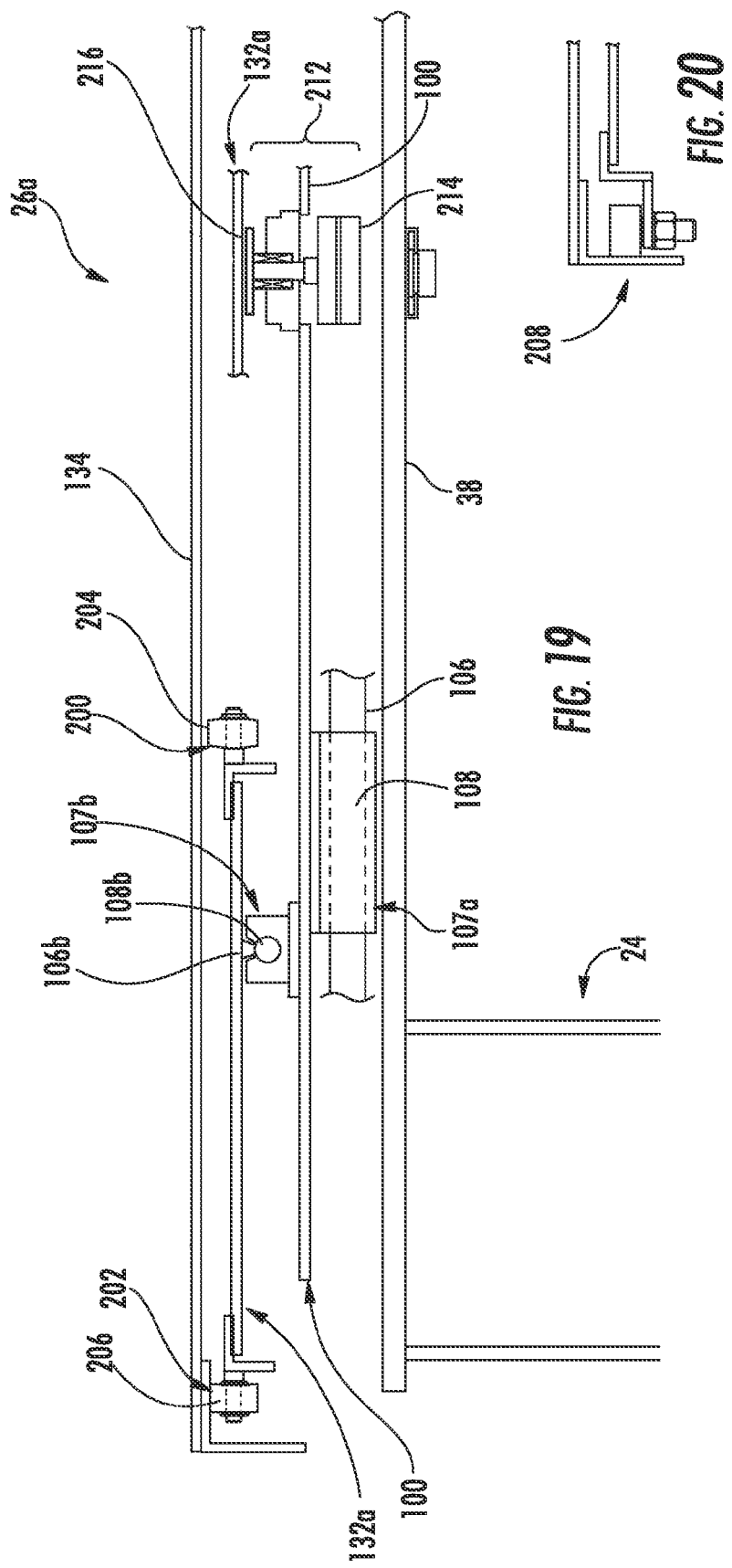

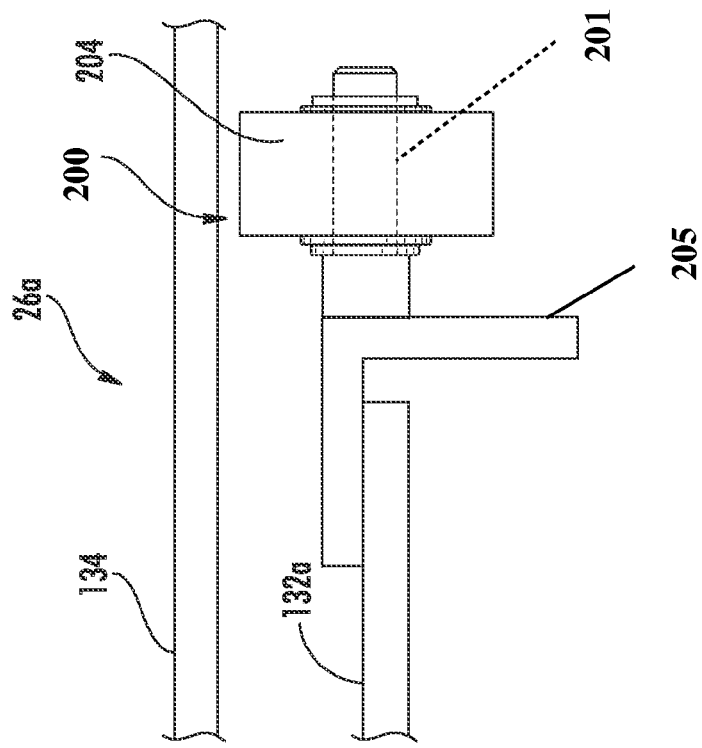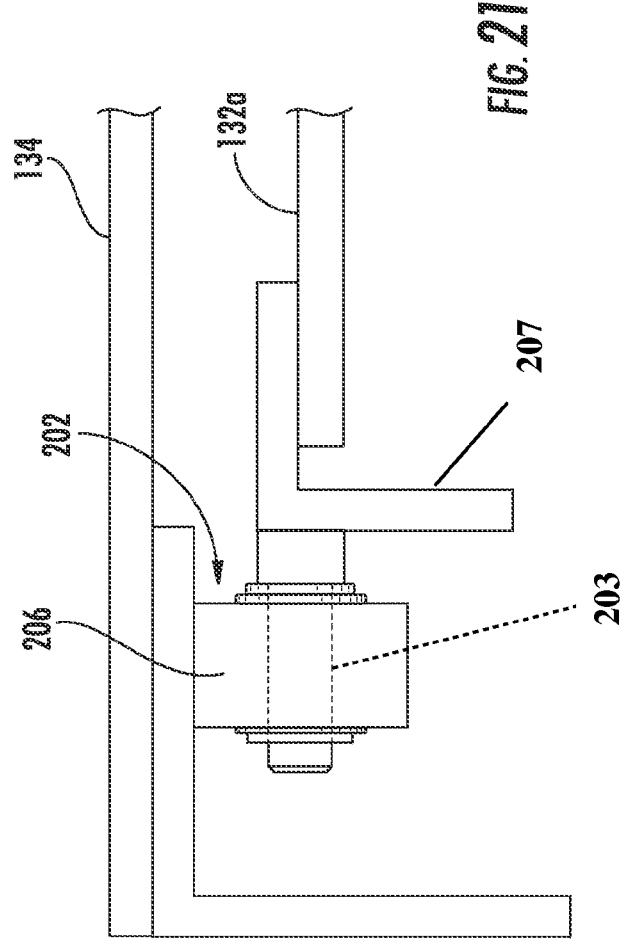
FIG. 21

EQUINE CT TABLE

CROSS REFERENCE TO RELATED APPLICATIONS

This application claims the benefit of U.S. Provisional Application No. 61/265,751, filed Dec. 1, 2009, and is also a continuation-in-part of application Ser. No. 12/358,186, filed Jan. 22, 2009, now abandoned, which claims the benefit of U.S. Provisional Application No. 61/011,960, each of which are incorporated herein by reference in their entirety.

BACKGROUND OF THE INVENTION

1. Field of the Invention

The present invention relates to the field of tables for use with diagnostic imaging systems and, more specifically, to an equine table for positioning a horse during a CT ("computed tomography") scan.

2. Description of the Related Art

Medical diagnostic imaging and scanning machines such as computed tomography imaging system (CT), positron and single photon emission computed tomography (PET and SPECT), to ultrasound and magnetic resonance imaging, spectroscopy and spectroscopy imaging (MRI, MRS and MRSI) are well known. Owing to good quality tomographic images with low dosage X-ray radiation, the CT system has become especially well accepted by the medical profession. Such machines are employed for combined imaging of soft tissue, bone and blood vessels and are useful in examining patients and aid in the diagnosis of injuries and indications, for example in identifying torn ligaments and tumors.

CT systems include a patient couch and an annular gantry having an outer ring secured to a stand and an inner ring mounted for rotation within the outer ring. During a scanning procedure, a patient lies on the couch which carries the patient in a step-wise or continuous fashion into a patient aperture of the gantry whereat the inner ring is rotated about the patient. Many components are supported by the gantry, which include an x-ray tube for providing the x-ray beam, one or more high voltage power supplies, balancing weights, a data acquisition module, and a bank of detectors diametrically opposed from the x-ray source. At least some of these components are secured to the inner ring for rotation therewith.

In order to obtain tomographic images of a patient, it is necessary that the patient be located exactly at a predetermined position inside the aperture of the gantry. It is also necessary that the patient be advanced in and retracted out of the gantry in predetermined movements. For this reason, CT systems are provide with a couch in which its vertical height may be adjusted to be in line with an axis of the aperture of the gantry and also axially moveable into and out of the aperture.

Several patient couches are known for this purpose. However, such couches are configured for human use and, thus, their use is limited to handling a range of sizes and weights associated with a majority of humans. Large animals, for example horses, would not fit on a conventional couch in a manner that would permit scanning of a leg or other body part. A horse's weight would also well exceed the typical 450 lbs load bearing capacity of a conventional couch. Further complicating matters is that a tranquillized horse is very difficult to precisely position, as is necessary for CT scanning.

Accordingly, what is needed in the art is a CT table that is suitable for carrying a horse. Also needed is for a table that allows for a horse to be accurately positioned during a CT examination. Moreover, there is a need for a table that communicates with the CT system by moving the horse in synchronization with the couch. Further needed is for the table to provide the aforementioned advantages without requiring electrical or mechanical attachments between the table and CT system.

BRIEF SUMMARY OF THE INVENTION

To achieve the foregoing and other objects, the present invention, as embodied and broadly described herein, provides various embodiments of an equine table for positioning a horse during a CT ("computed tomography") scan.

In the broadest sense, the invention is a radiation system for the examination and/or treatment of large animals, such as a horse, having a table capable of supporting and carrying the large animal. The table includes a frame positionable over a couch, a carousel carried by the frame and configured for placement of the large animal thereon and a motion tracking system carried by the frame. The motion tracking system detects movement of the couch and transmits signals to an actuating system when the couch moves whereupon the actuating system causes the carousel to move, preferably in synchronized motion, when the couch moves. The motion tracking system includes a magnet that moves with and is carried by the couch and a transducer that communicates with the magnet as the couch moves in order to produce the signals. Alternatively, the motion tracking system includes a laser directed at the couch to detect movement of the couch and a transducer that communicates with the laser as the couch moves in order to produce the signals. The actuating system includes a motor to drive the carousel and at least one track secured to the frame, which the carousel travels on when being driven by the motor. The table includes at least one cantilever attached to the carousel for carrying an appendage of the large animal. The cantilever is manually moveable and infinitely positionable around the perimeter of the carousel. The carousel includes a base plate, a top plate and a template positioned between the base and top plates. The template retains at least one ball bearing which is sandwiched between the base and top plates such that the top plate is moveable independent of and relative to the frame and base plate. The top plate can be manually moved radially and linearly relative to the frame by having an operator manually apply a force thereto. A docking system having a rail may also be provided. The table includes a castor having a notch which communicates with the rail for positioning of the table to the couch.

In the broadest sense, the invention is a table for use in the examination and/or treatment of a large animal. The table includes a frame configured to be positionable over a CT couch and capable of supporting the weight of the large animal and a carousel carried by the frame and configured for placement of the large animal thereon. The carousel includes a base plate, a top plate and a template disposed between the base and top plates. The template retains a plurality of ball bearings which rest on top of the base plate. And, the top plate rests on the ball bearings. The ball bearings allow for the top plate to be manually moved linearly and radially relative to the base plate and frame for positioning of the large animal. The table further includes at least one cantilever attached to the carousel for carrying an appendage of the large animal. The cantilever is manually and infinitely positionable around the perimeter of said carousel. The carousel includes a channel into which a tongue of the cantilever is received for releaseable attaching the cantilever to the carousel. The carousel also includes a lock which is moveable between a first position spaced away from the top plate such that the top plate is moveable relative to said base plate and a second position engaged against the top plate such that the top plate is restricted from being moved relative to the base plate. The table further includes a motion tracking system which detects movement of the couch and transmits signals to an actuating system based on movement of the couch. The actuating system causes the carousel to move in synchronicity with the couch.

BRIEF DESCRIPTION OF THE DRAWINGS

The above described and other features, aspects, and advantages of the present invention are better understood when the following detailed description of the invention is read with reference to the accompanying drawings, wherein:

FIG. 3 is a detail of the equine table of FIG. 1, showing a leg of the table in a lowered position;

FIG. 4 is a detail of the equine table of FIG. 1, showing a leg of the table in a raised position;

FIG. 12 is a top view of an alternative embodiment of the invented equine table, comprising the same elements as that described with regards to the FIGS. 1-11 except for the carousel which has a different configuration, the top plate (uppermost plate) being partially removed for clarity, in accordance with an exemplary embodiment of the present invention;

FIG. 13 is a fragmented side sectional view of the carousel taken along section line 13-13 of FIG. 12, showing elements of the alternative embodiment;

FIG. 14 is a fragmented side sectional view of the carousel taken along section line 13-13 of FIG. 12, showing elements of the alternative embodiment;

FIG. 15 is fragmented side sectional view of the carousel taken along section line 15-15 of FIG. 12, showing elements of the alternative embodiment;

FIG. 16 is a top view of a detail showing a rotational centering bearing assembly;

FIG. 17 is a side view of the detail of FIG. 16;

FIG. 19 is an enlarged view of FIG. 13;

FIG. 20 is an enlarged view of FIG. 17;

FIG. 21 is a partial, enlarged view of FIG. 13, showing the inner and outer roller assemblies;

DESCRIPTION OF THE PREFERRED EMBODIMENTS

The present invention will now be described more fully hereinafter with reference to the accompanying drawings in which preferred embodiments of the invention are shown. This invention may, however, be embodied in many different forms and should not be considered as limited to the embodiments set forth herein. These exemplary embodiments are provided so that this disclosure will be both thorough and complete, and will fully convey the scope of the invention to those skilled in the art.

Figure 1:
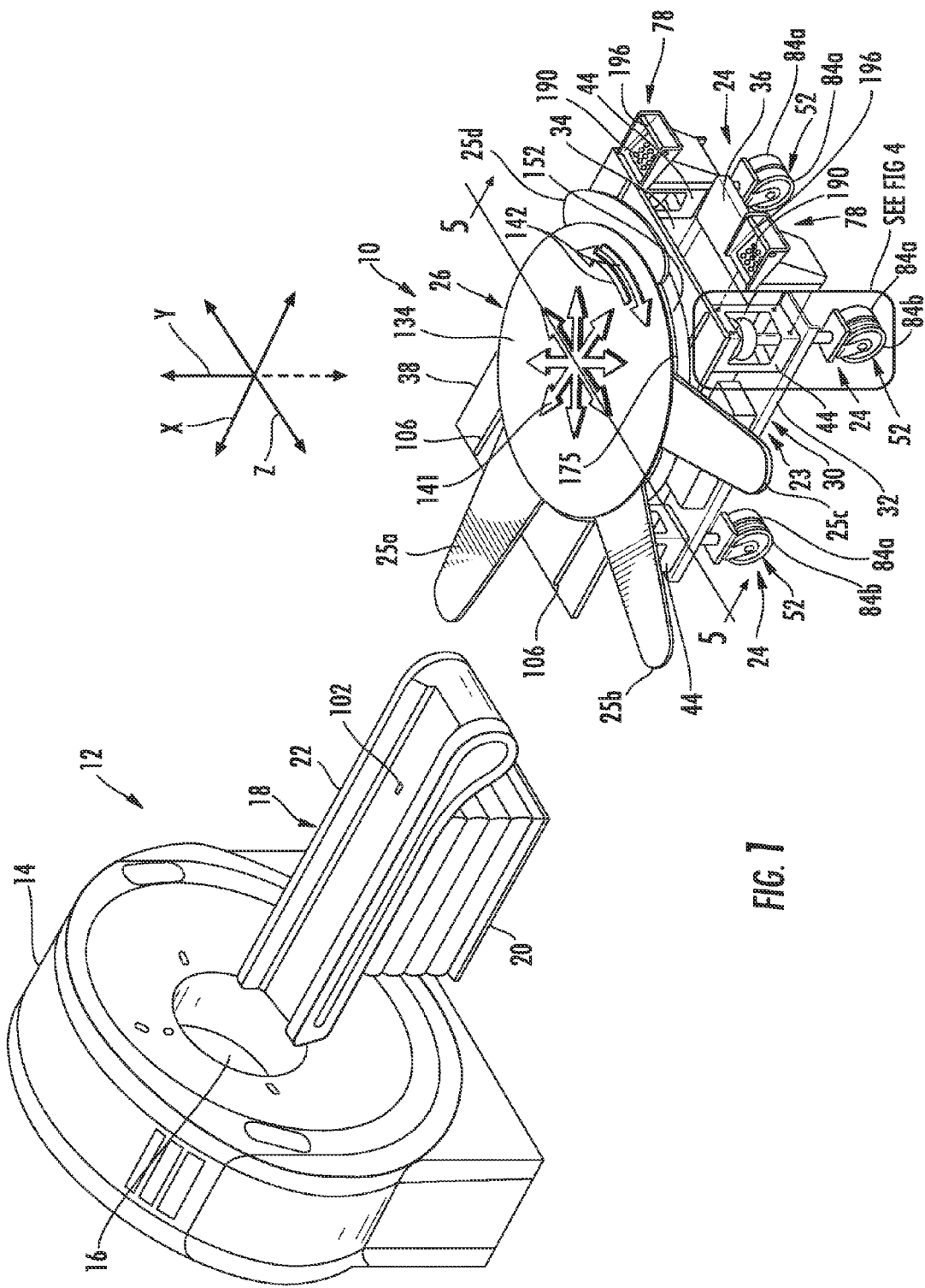
FIG. 1 is a perspective view of the invented equine table shown with a CT imaging system, in accordance with an exemplary embodiment of the present invention.
Figure 2:
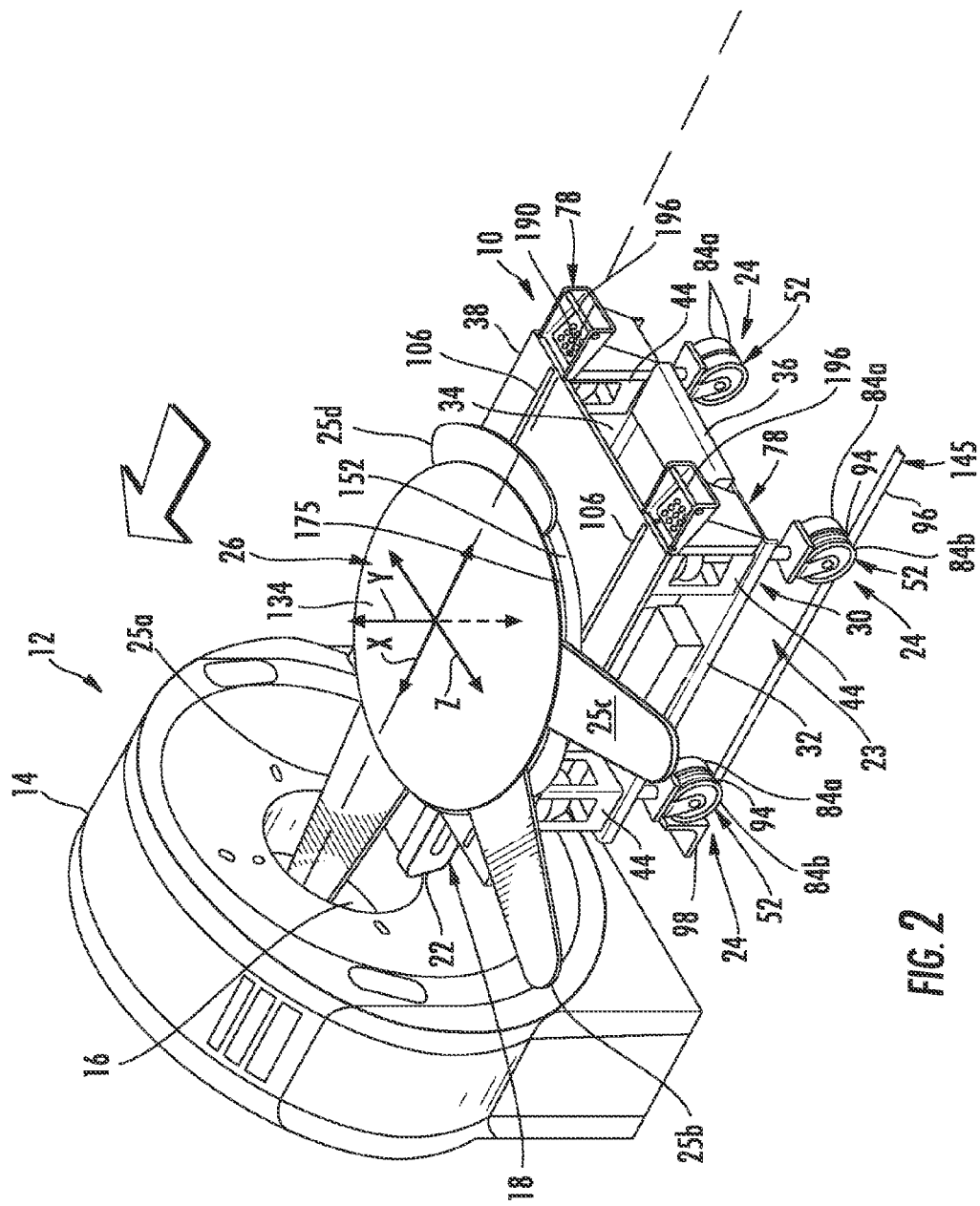
FIG. 2 is a perspective view of the equine table of FIG. 1 in communication with a CT imaging system.

Referring to the drawings, and particularly to FIGS. 1 and 2, the present invention is an equine table 10 for use with radiation diagnosis and/or therapy systems (collectively "radiation system"), such as computed tomography imaging system (CT), positron and single photon emission computed tomography (PET and SPECT), to ultrasound and magnetic resonance imaging, spectroscopy and spectroscopy imaging (MRI, MRS and MRSI). Without limiting the table 10 to use with a particular system, the description herein is in reference to a conventional CT imaging system 12.

The exemplary CT system 12 includes multiple computers that control the entire CT system 12, a gantry 14 with a patient aperture 16, and a patient couch 18 comprising a base portion 20 and a top portion 22. The gantry 14 and couch 18 have multiple microprocessors (not illustrated) that control the rotation of the gantry 14, movement of the couch 18 (up/down and in/out), tilting the gantry 14 for angled images, and other functions such as turning the x-ray beam on and off. A dedicated computer reconstructs the raw CT data into a combined image of soft tissue, bone and blood vessels. A workstation with dedicated controls allows a technologist to control and monitor the process.

The conventional CT system 12 is configured for the examination of humans and not for large animals such as a horse. Thus, limitations as to the overall size and weight of a patient that the patient couch 18 can support and accurately position during an examination generally corresponds to a range associated with humans. For example, the load capacity of the couch 18 is typically at about 450 pounds; suitable for most humans but vastly insufficient to handle the typical weight of a horse. Likewise, due to the overall size of a horse, the conventional couch 18 is unable to properly position the horse within the aperture 16 of the gantry 14 during examination.

To overcome weight and size limitations in conventional patient handling, the invented table 10 is uniquely configured to support and accurately position large animals, such as horses, during a CT examination. Although the table 10 is principally contemplated for use with horses, it is to be understood that the invention may also be suitably used with other large animals. Further, it is to be understood that the invented table 10 may have application with humans who do not easily fit on, or are in excess of the load bearing capacity of, a conventional couch 18. Persons and animals that may use the invented table 10 are collectively described herein as "patients". As the invention is contemplated for being used principally with horses, the description of the patient herein is in reference to a horse.

The invented table 10 is uniquely configured to carry and position a full sized horse, and to communicate with the CT system 12 for synchronized movement with the couch 18, during the examination. More specifically, the table 10 has a frame 23 providing structure sufficient to support a horse, a system of legs 24 for moving and raising/lowering the table 10, a plurality of cantilevers 25a-25d for carrying appendages (e.g. head, rump, rear legs and front legs) of the horse, a carousel 26 for positioning the horse prior to and during scanning, and motion tracking and actuating systems 27, 28 (FIGS. 10 and 9, respectively) that communicate with the CT system 12 for synchronized movement of the horse with the couch 18 during the examination.

The frame 23 comprises a U-shaped base 30 having left, right and rear members 32, 34, 36, a platform 38 for carrying the motion tracking system 27 (see FIG. 10) and the carousel 26, and supports 44 affixed between and joining the base 30 to the platform 38. The U-shaped base 30 has an open front and the platform 38 is vertically positionable to a height whereby the table 10 can be positioned over the couch 18.

Referring to FIGS. 3 and 4, each leg 24 include a height adjustment system 46 and a castor assembly 52. In the preferred embodiment, the height adjustment system 46 includes an air spring 48 and a spindle assembly 50 that cooperate together in order to raise and lower the table 10 to a desired height. For example, it is desirable to have the table 10 in a lowered position when loading a horse on the table 10. This is particularly important where a low ceiling height would otherwise limit functionability of hoist system (not shown), which is typically used when loading a horse onto and off of the table 10. Thereafter, the table 10 would be returned to a raised position whereby it could be positioned, with a predetermined amount of clearance, over the couch 18 for commencement of the examination. The ability to raise and lower the height of the table 10 allows of the invention to be used with any fixed or variable height CT system 12. Not to be construed as limiting, in an exemplary embodiment the height adjustment system 46 allows for about six inches of vertical travel to achieve these advantages.

The air spring 48 is sandwiched between an upper plate 54, that is affixed to the support 44, and the spindle assembly 50. The air spring 48 is of a conventional configuration, having inflatable members sandwiched between end retainers.

The spindle assembly 50 is positioned between the air spring 48 and castor assembly 52. The spindle assembly 50 includes an upper plate 56 attached to the air spring 48, a lower plate 66 attached to the castor assembly 52, a shaft 58 extended between the upper and lower plates 56, 66 whereby the shaft 58 fixes the distance between and joins together the air spring 48 and castor assembly 52, and a spindle 60 moveably mounted on the shaft 58 and having linear bearings 62 for aiding in said movement. The spindle 60 has a flanged lower end 64 that is attached the frame base 30 whereby the spindle 60 respectively increases and decreases in height with the table 10. To eliminate relative rotation between, the spindle 60 and shaft 58, a key way system (not shown) may be provided. Rubber bumpers 80 are provided between the flange 64 and lower plate 66 to reduce impact when lowering the table 10.

Figure 7:
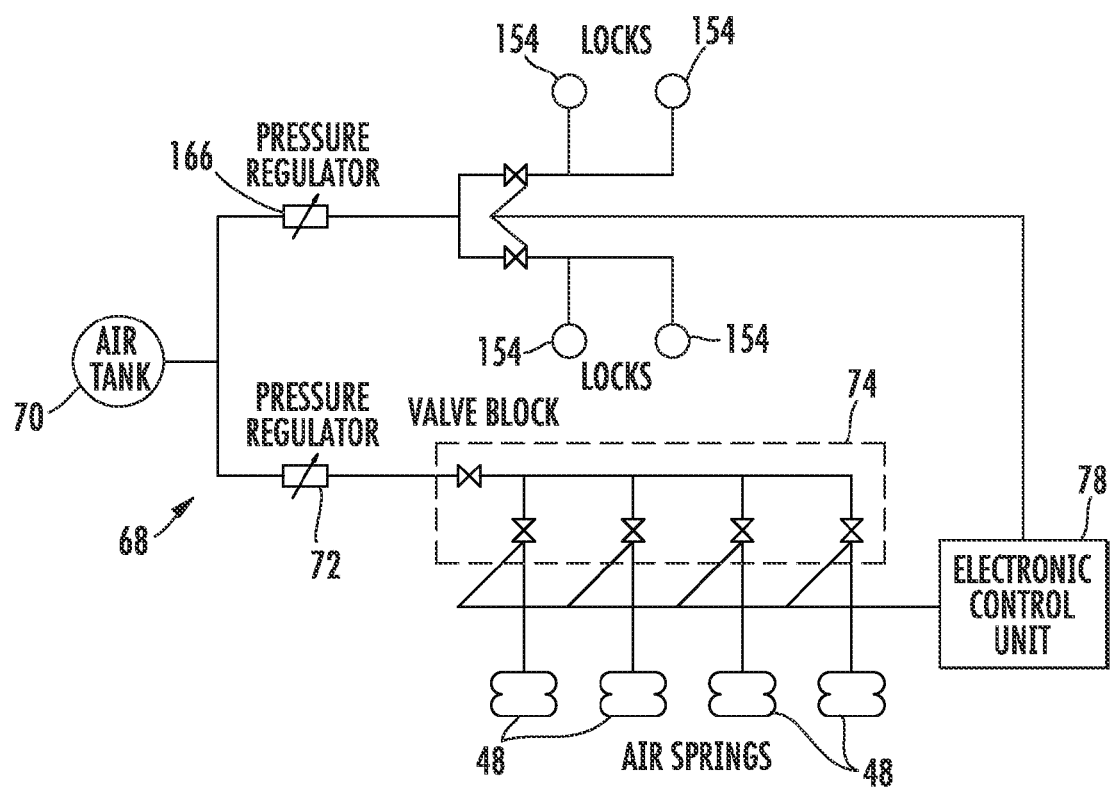
FIG. 7 is a schematic of a pneumatic system for operating air springs and various locking mechanisms of the equine table.

Referring to FIG. 7, an air supply system 68 delivers compressed air to inflate the air springs 48 to increase the height of the table 10 (fee FIG. 4). The air supply system 68 comprises an air compressor 70, a pressure regulator 72, a valve block 74, connecting piping 76 (see FIGS. 3 and 4), and an electronic control unit 78 (see also FIG. 1) to control the delivery to and release of air from the air springs 48.

In operation, compressed air is supplied to the air springs 48, causing the inflatable members to increase in volume and height as illustrated in FIG. 4. The air springs 48 push the respective upper plates 54 upward thereby lifting the frame 23 (i.e. the supports 44, base portion 20 and platform 38), spindle 60, and carousel 26.

The spindle assembly 50 provides stops for upward and downward travel of the table 10. During inflation of the air springs 48, the spindle 60 is carried upwards (indicated by the arrow in FIG. 4) with the frame 23 until the spindle 60 engages the upper plate 56. During deflation of the air springs 48, the frame 23 lowers (indicated by the arrow in FIG. 3) carrying the spindle 60 until it engages the bumpers 80 mounted on the lower plate 66.

Although a preferred embodiment of a height adjustment system 46 is described herein, those skilled in the art would appreciate that other system may be used. For example, a scissor lift system has been described in the prior art for use with a patient couch, such as that described in U.S. Pat. No. 4,613,122 to Yoshinori Manabe. Notwithstanding, it is believed that the presently described height adjustment system 46 provides improved height control and stability that is desirable under the substantial load conditions experienced when positioning a horse.

Referring to FIG. 1, the castor assemblies 52 allows an operator to manually move the table 10 along the floor and to dock the table 10 to the CT system 12. Referring to FIGS. 3 and 4, each castor assembly 52 includes a bracket 82, at least one castor (two different types of castors 84a, 84b are illustrated) is disposed within the bracket 82 and rotatably mounted on a shaft 86. In the preferred embodiment, the bracket 82 includes at least one upper plate 87 that is affixed to the spindle assembly lower plate 66 and left, right and center members 88, 90, 92 for securing the shaft 86 and maintaining the castors 84a, 84b. The members 88, 90, 92 are provided with openings through which the shaft 86 is received and secured by bolts or other conventional means. The castors 84a, 84b are rotatably secured to the shaft 86. It is to be understood that other bracket assemblies may be used. For example, the bracket assembly may include a different number of castors (e.g. one castor) from that illustrated herein and the number of bracket members (e.g. left and right members only) may correspondingly also differ. Nevertheless, the preferred embodiment allows for simultaneous application of two different types of castors 84a, 84b and provides additional structural integrity.

Referring to FIG. 2 (see also FIGS. 3 and 4), in the preferred embodiment, a pair of legs 24 has conventional cylindrical castors 84a (illustrated on the right side of the table 10), whereas the opposed pair of legs 24 (illustrated on the left side of the table 10) has two different types of castors 84a, 84b with one castor 84a being of a conventional cylindrical shape and the other castor 84b being cylindrical but further having a notch 94 formed in along its circumference for communication with an optional docking system 145.

Referring to FIG. 2, the docking system 145 comprises a rail 96 and a stop 98 to provide a method for quickly, consistently and accurately positioning the table 10 in relation to the CT system 12. To dock the table 10, it is maneuvered onto the rail 96 then pushed forward until engagement with the stop 98. To maintain the table 10 on the rail 96, the rail 96 fits within the notch 94 of the castors 84b. The notch 94 and rail 96 are complementary in size and shape, for example, the illustrated rail 96 has a triangular cross section which fits within the V-shaped notch 94 (see FIGS. 3 and 4). It is to be understood that rails and notches of other shapes and sizes may also suitably be used.

Figure 9:
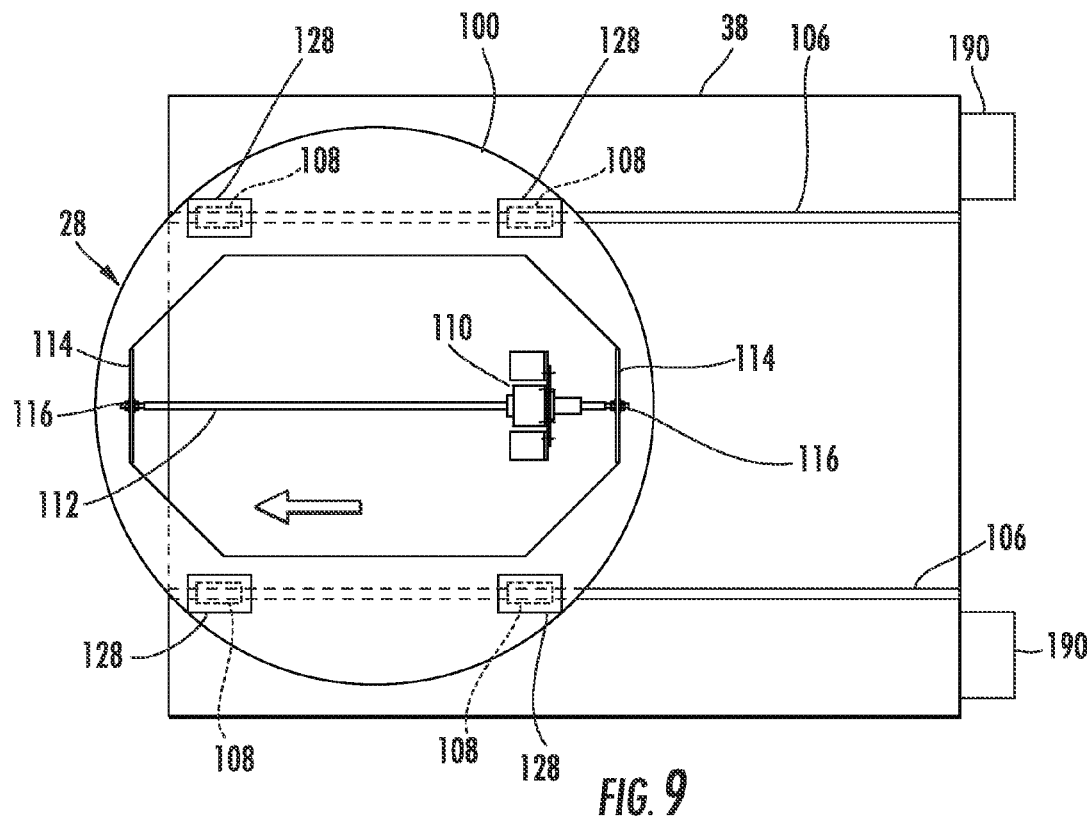
FIG. 9 is a top view of the equine table of FIG. 1, with the carousel removed, showing the carriage in a forward position and a linear movement system for advancing and retracting a patient in relation to a CT imaging system.
Figure 10:
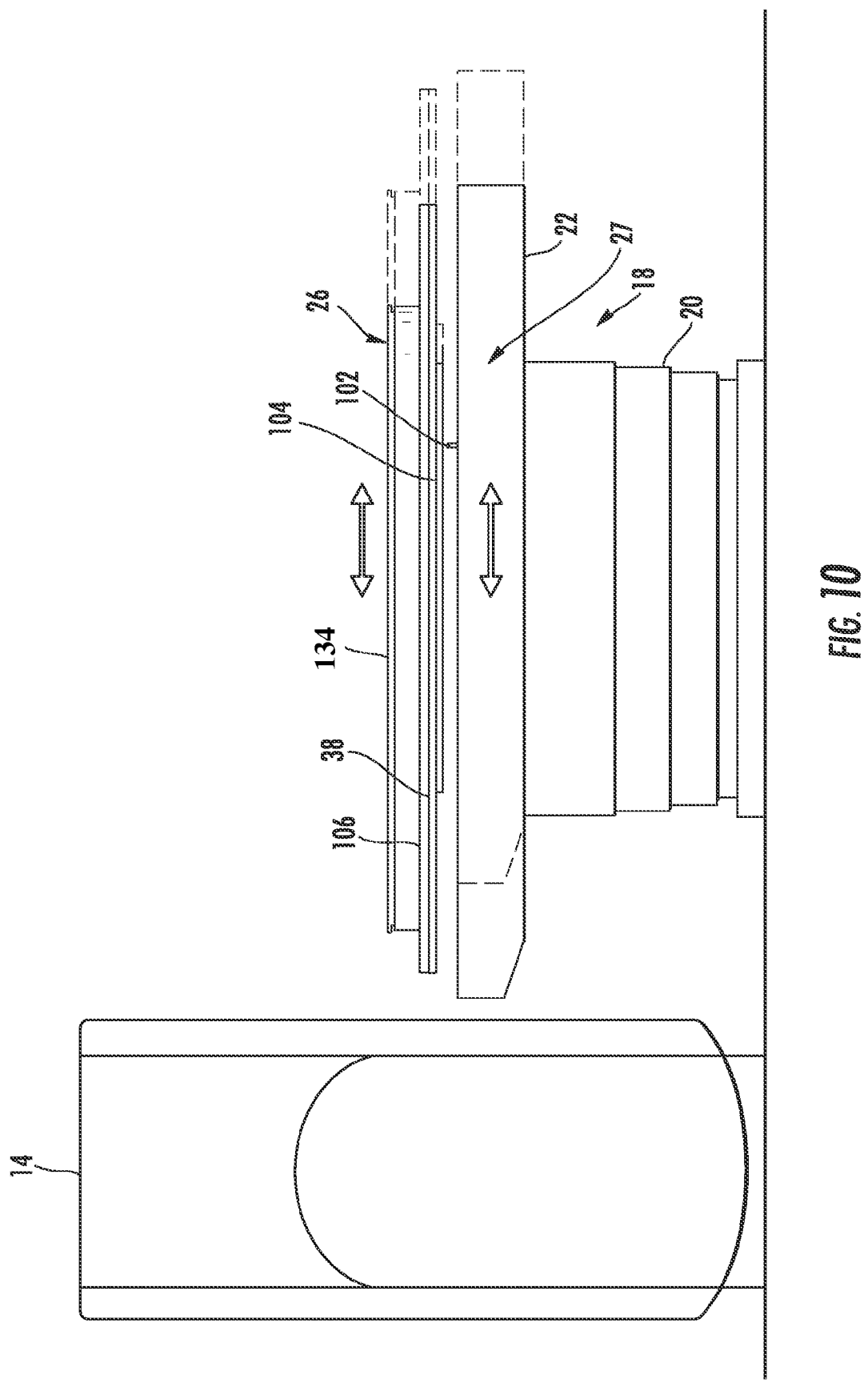
FIG. 10 is a partial side view equine table and CT imaging system of FIG. 2, but with the cantilevers removed for clarity and showing the carousel of the equine table moving in synchronization with the patient couch.

Referring to FIG. 10, the motion tracking system 27 determines movement (speed, direction and distance) of the couch 18 and communicates with the actuating system 28 (FIGS. 8 and 9) to synchronize movement of a carriage 100, (and, i.e., the horse), with that of the couch 18. The motion tracking system 27 comprises a magnet 102 (see also FIG. 1) that coextensively moves with and is carried by the couch 18 and a transducer 104 attached to the bottom of the carriage 100 and being disposed vertically above the magnet 102. Thus, movement of the couch 18 causes the transducer 104 to vary its output voltage in response to changes in magnetic field caused by the moving magnet 102. A resulting electric current is sent to computer which signals the actuating system 28 to mimic the movement of the couch 18.

Figure 8:
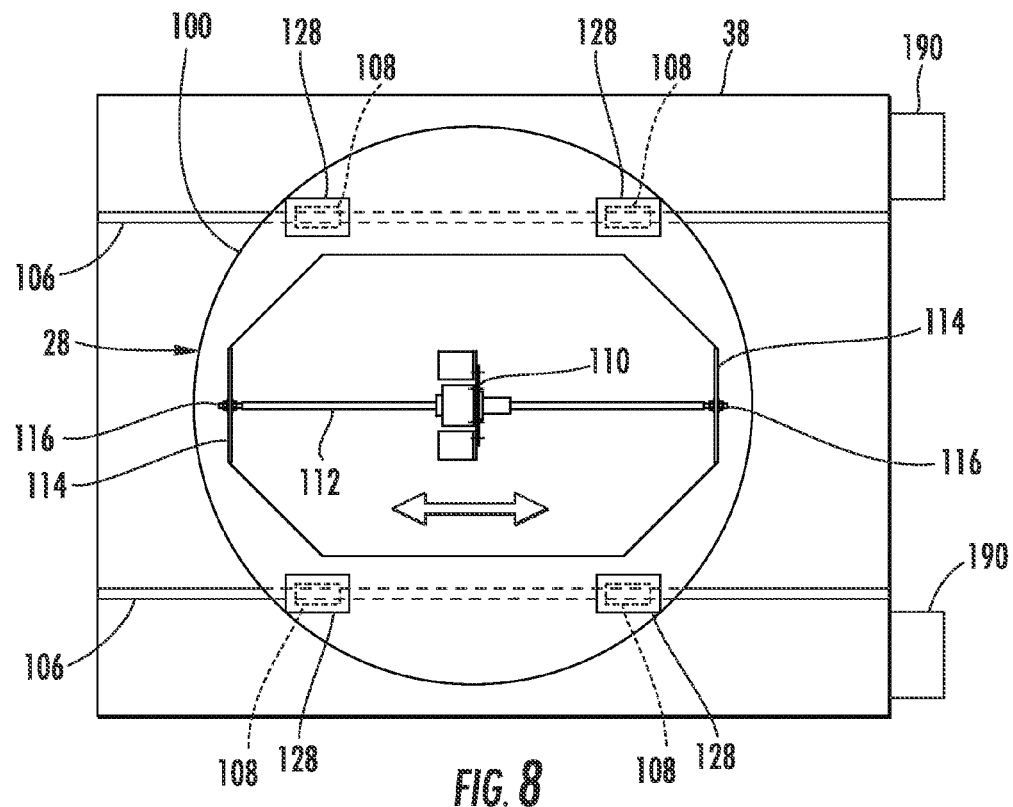
FIG. 8 is a top view of the equine table of FIG. 1, with the carousel removed, showing the carriage in a neutral position and a linear movement system for advancing and retracting a patient in relation to a CT imaging system.

Referring to FIGS. 8 and 9, the actuating system 28 comprises a pair of tracks 106 (see also FIGS. 1 and 2) secured to the platform 38; the carriage 100 having an open interior and moveably mounted on the tracks 106 by linear bearings 108; a motor 110 positioned within the carriage interior and affixed to the platform 38 wherein the motor 110 drives a rotatable shaft 112 which is attached at opposed ends to bulkheads 114 provided in the carriage 100. The shaft 112 has suitable fittings 116 at the shaft-bulkhead interface to secure the shaft 112 while permitting rotation relative to the bulkheads 114. Although a rotary motor is described herein, other suitable motor configurations could be used such as a linear motor.

The actuating system 28 receives electrical signals that correlate to movement detected by the motion tracking system 27 (FIG. 10), causing the motor 110 to drive the shaft 112. As the motor is fixed to the platform 38, the carriage 100 is caused to move linearly along the tracks 106 mimicking forward and rearward movement of the magnet 110 and, i.e., the couch 18, as illustrated in FIG. 10. In this manner, handling of a horse requires no operational changes to the conventional CT system 12. Additionally, no mechanical or electrical attachment is necessary between the table 10 and the CT system 12. For purposes of this application, the attachment of a magnet 102 to the couch 18 is not considered to be an electrical or mechanical attachment between the couch 18 and table 10. Thus, the couch 18 would be operated, and enter and be retrieved from the gantry 14, in a conventional manner.

It is contemplated that tracking and/or actuating systems other than that described in the preferred embodiment may be used. For example, the motion tracking system may comprise a laser system (not illustrated) mounted to the bottom of the carriage 100, wherein a laser would be trained to the rear of the couch 18 to track movement thereof. A transducer would create an electrical signal based on the detected change in speed, direction and distance between the laser and couch, causing the motor 110 to mimic movement of the couch 18.

Figure 5:
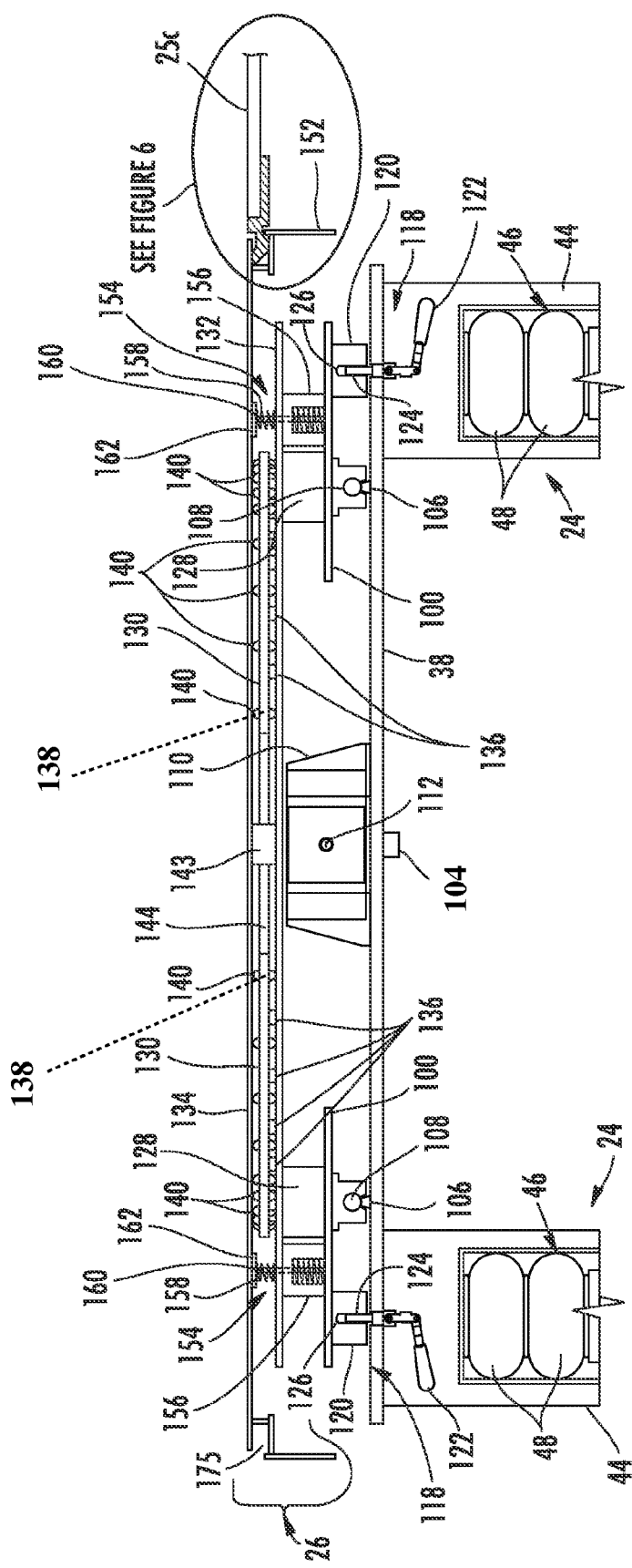
FIG. 5 is a sectional view of the equine table, taken along section line 5-5 of FIG. 1.

Referring to FIG. 5, to keep the carriage 100 from moving during transport of the table 10 and during loading/unloading of the horse, locks 118 are provided to secure the carriage 100 to the platform 38. The locks 118 include a lever system mounted to the platform 38 and a block 120 mounted to the carriage 100. The lever system includes a handle 122 that when manually pulled causes a pin 124 to extend into an opening 126 in the block 120 thereby releasably fixing the platform 38 and carriage 100 together.

Figure 11:
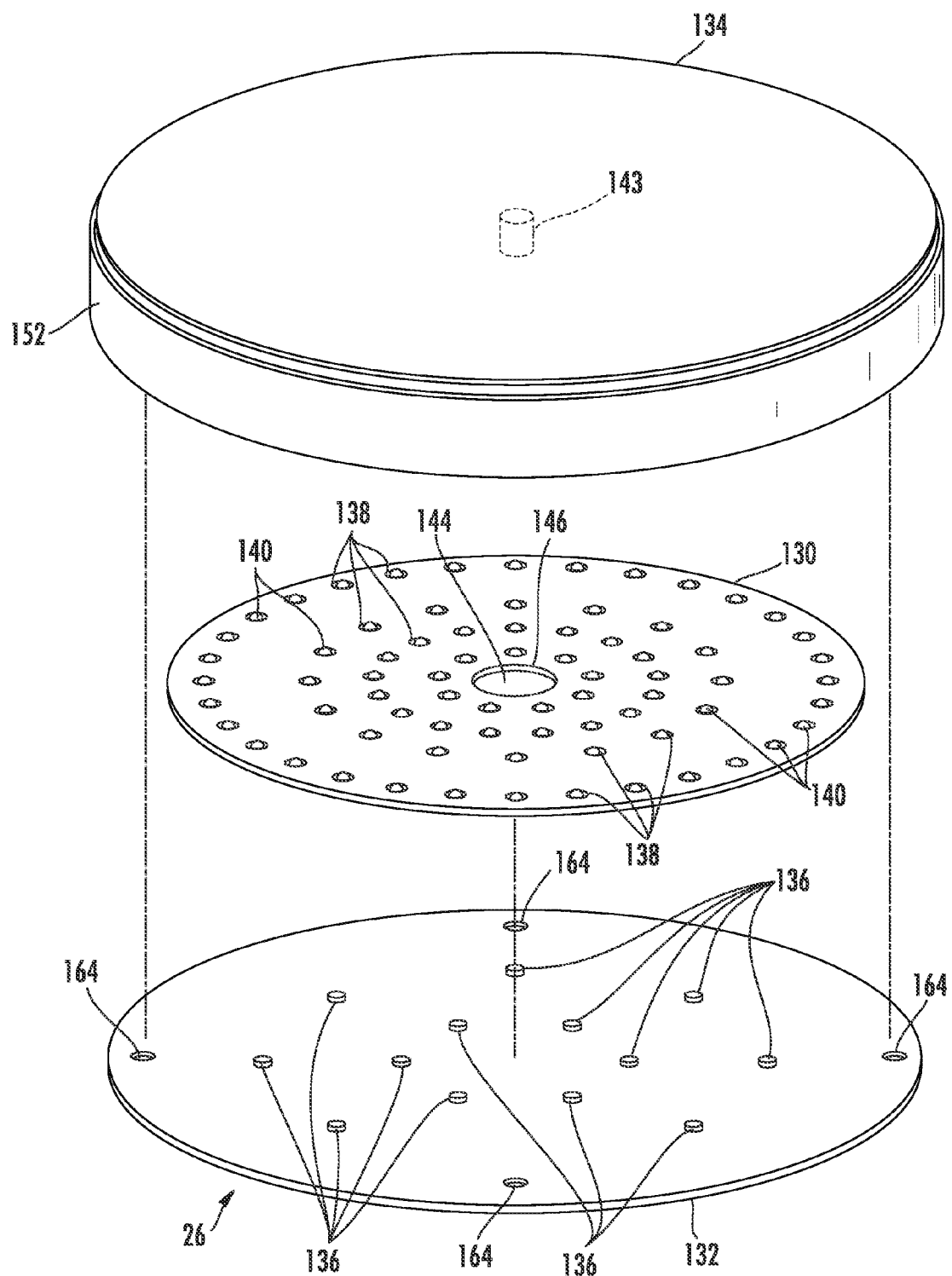
FIG. 11 is an exploded view of the carousel of the equine table of FIG. 1.
Figure 18:
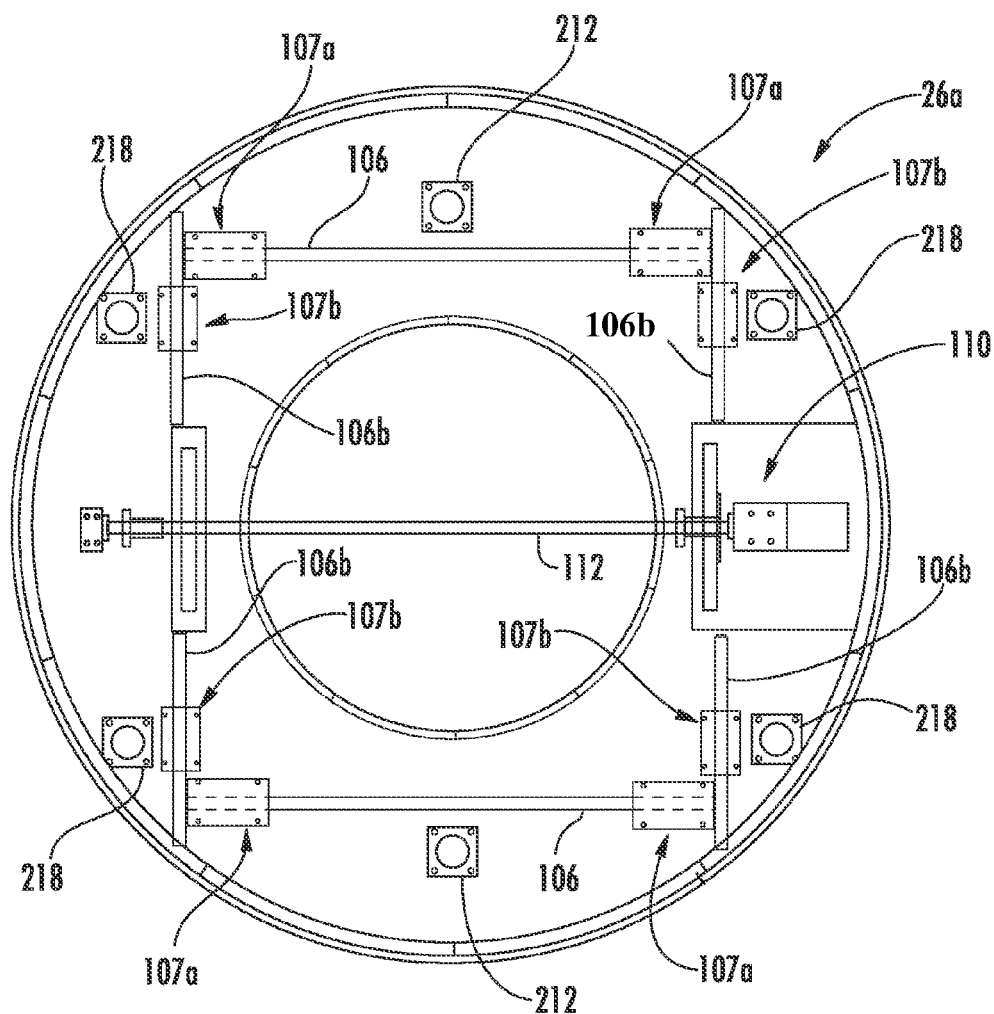
FIG. 18 is a top view of the carousel of FIG. 12 showing positioning of the linear bearing assemblies and lock assemblies.
Figure 22:
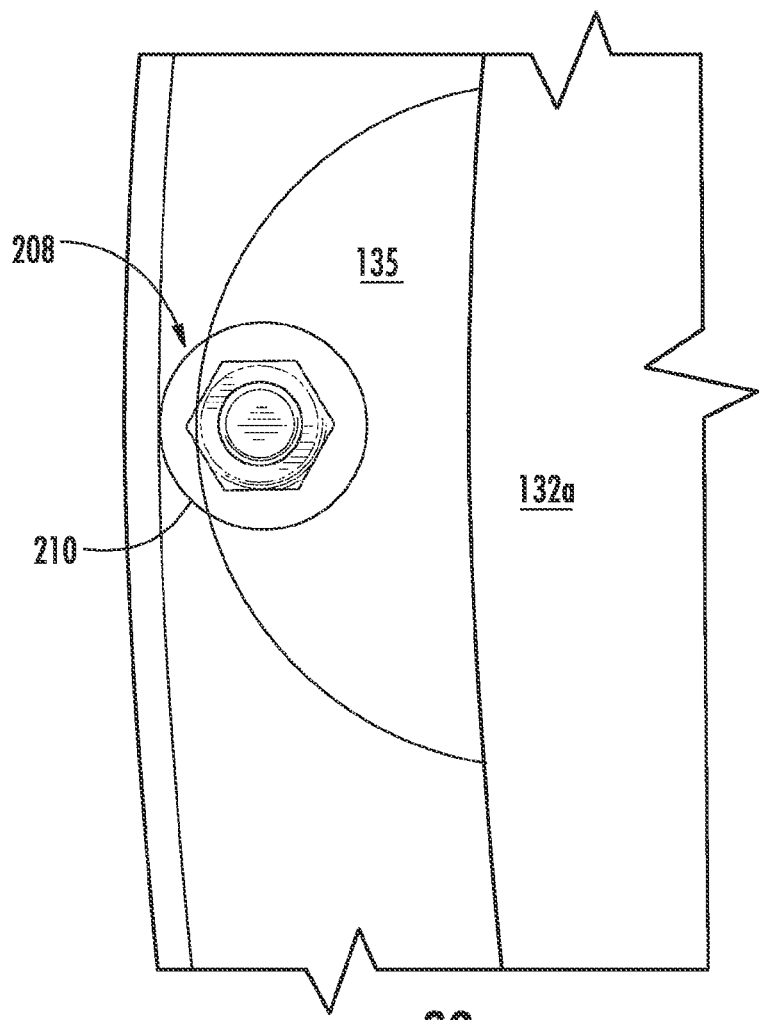
FIG. 22 is an enlarged view of FIG. 16.
Figure 23:
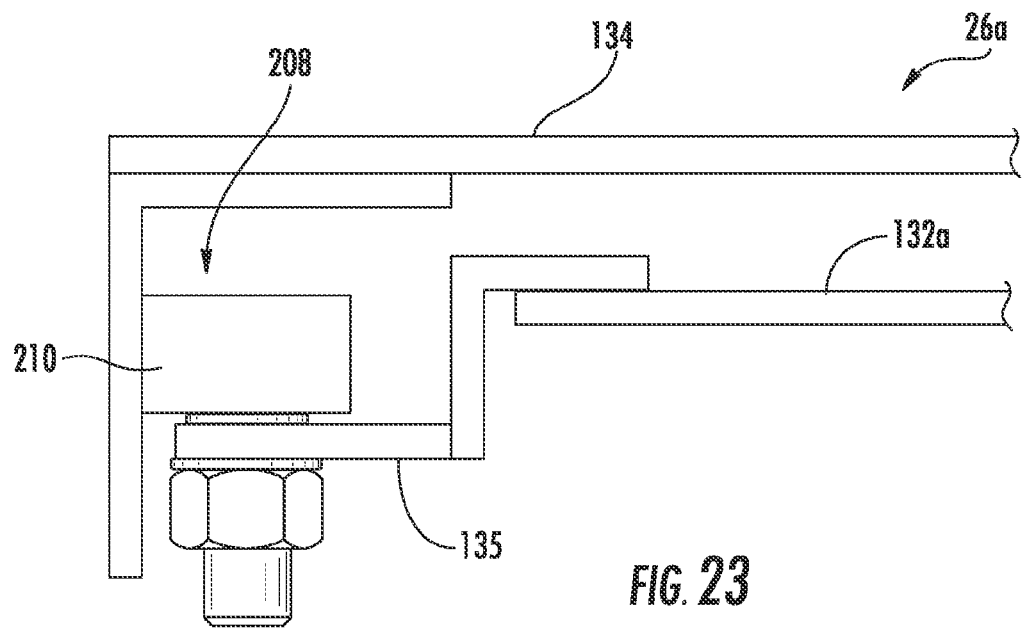
FIG. 23 is an enlarged view of FIG. 17.
Figure 24:
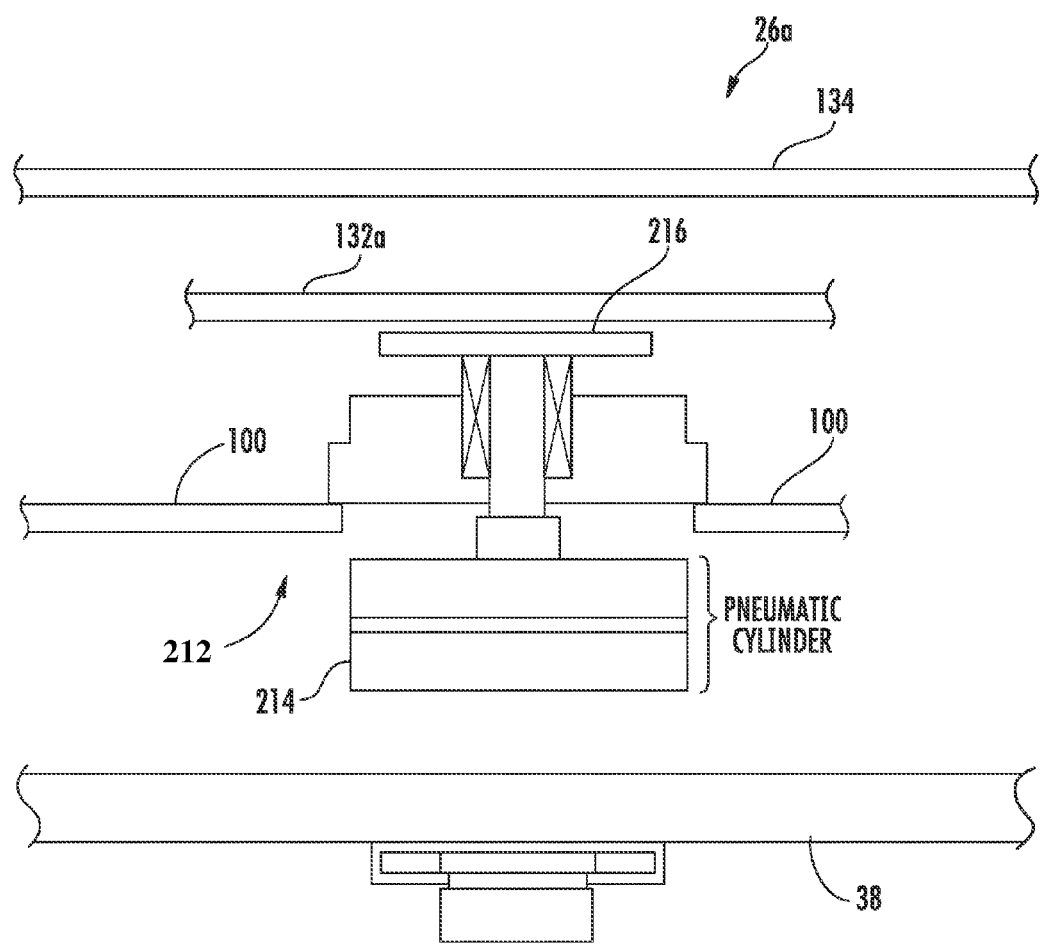
FIG. 24 is a detail of the transverse lock assembly of FIG. 13.
Figure 25:
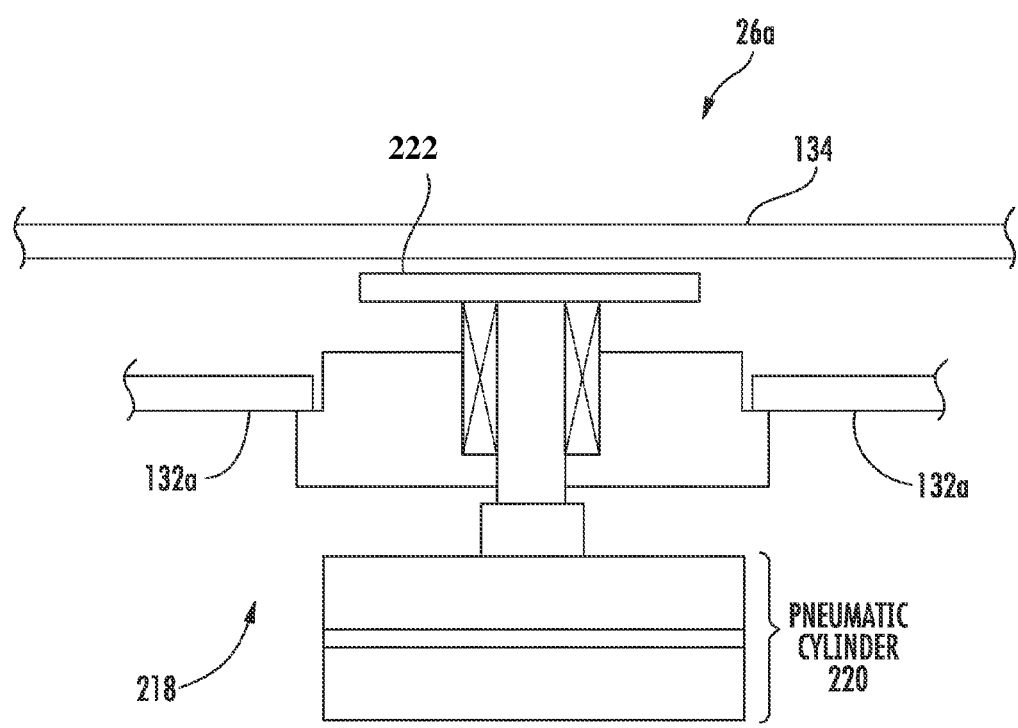
FIG. 25 is a detail of the rotational lock assembly of FIG. 13.

Supports 128 (see also FIGS. 8 and 9) are mounted on the carriage 100 to support the carousel 26 in clearance above the motor 110. Referring to FIGS. 5 and 11, the carousel 26 comprises a template 130 disposed between base and top plates 132, 134. The base plate 132 is attached to the supports 128 and forms the base of the carousel 26. The base plate 132 and template 130 are affixed together by spacers 136, which are mounted there-between to position the template 130 at a predetermined height in relation to the base plate 132. The template 130 is provided with a plurality of openings 138 into which ball bearings 140 are disposed. The ball bearings 140 are sized to extend equally above and below the template 130 such that the ball bearings 140 (only a few of the openings 138 and ball bearings 140 are labeled in FIGS. 5 and 11) rest on the base plate 132, whereas the top plate 134 rest on the ball bearings 140. The top plate 134 forms the surface upon which the horse is supported (see also FIGS. 1 and 2). It is to be understood that a cushioning material such as foam, pad(s) or the like (not illustrated) is positioned on the top plate 134 to protect the horse's circulatory and neurological systems.

By being positioned on the ball bearings 140, the top plate 134 may be manually moved linearly in any direction (indicated by arrows 141 in FIG. 1; see also FIG. 2) in a horizontal x-z plane and any angle radially (indicated by arrows 142 in FIG. 1) in angular (i.e. radial) motion about a vertical axis Y (yaw) of the table 10. Annular and linear movement of the top plate 134 is independent of the remaining portions of the table 10 whereby the top plate 134 may be selectively moved forward, rearward, left or right, or at any angle there-between, or radially, with respect to remaining table components (e.g. the frame 23, legs 24, actuating systems 28, base plate 132, template 130, etc.), docking system 145 (FIG. 2) and CT system 12 (e.g. the gantry 14 and couch 18).

Referring to FIG. 11, an exemplary embodiment the template 130 is provided with eighty openings 138, each containing one ball bearing 140. Under a load of 3,500 lbs (which includes the weight of a 2,200 lb horse and 1,300 lbs for the top plate 134), the load on each ball bearing is 43.75 lbs. It is estimated by the inventor that the top plate 134 and horse may be repositioned in relation to the remaining table components by application of about 15 lbs of force. As such, an operator may easily position and reposition a horse in preparation for examination.

Although there is no limit to the range of radial motion through which the top plate 134 may be rotated, i.e. any degree of rotation up to and beyond 360 degrees, the relative linear motion between the top plate 134 and remaining table components is restricted to a maximum distance. This maximum travel distance is determined by a shaft 143 that extends from the top plate 134 into an opening 144 in the template 130. The diameter of the opening 144 is greater than that of the shaft 143 so that the shaft 143 may move within the opening 144 a distance before engaging the interior surface 146 defining the opening 144. Not to be construed as limiting, in an exemplary embodiment the maximum permitted amount of travel of the shaft 143 within the opening 144 corresponds to five inches of linear movement of the top plate 134.

The top plate 134 further includes a skirt 152 to protect against equipment damage and injury to the operator and horse. In an alternative embodiment, the top plate 134 is not provided with the shaft 143. Instead, linear movement of the top plate 134 in the x-y plane is limited by the amount of free play between the skirt 152 and top plate 134 or carousel 26.

Referring to FIG. 5, locks 154 are provided to secure the top plate 134 in a selected position. Each lock 154 includes a piston assembly having a cylinder 156, a shaft 158, a spring 160 disposed on the shaft 158, and a contact pad 162. The piston assembly is attached to the carriage 100 with the shaft 158 extending through an opening 164 (FIG. 11) in the base plate 132 to the top plate 134.

Referring to FIG. 7, the locks 154 are pneumatically operated. A schematic of the air delivery system 68 is illustrated comprising a compressor 70, pressure regulator 166, pneumatic cylinder locks 154, piping, and electronic control unit 78. Referring to FIG. 5, to release the top plate 134 for movement relative to the remaining table components, compressed air is delivered to the locks 154 causing the shaft 158 to retract from the top plate 134 such that the top plate 134 rests fully on the ball bearings 140. During the retracting process, the springs 160 are caused to compress and store potential energy. To lock the top plate 134 in a position, compressed air is released such that the springs 160 urge the pads 162 upwards against the top plate 134. The frictional engagement between the pads 162 and top plate 134 maintains the top plate 134 from moving relative to the remaining table components.

Figure 6:
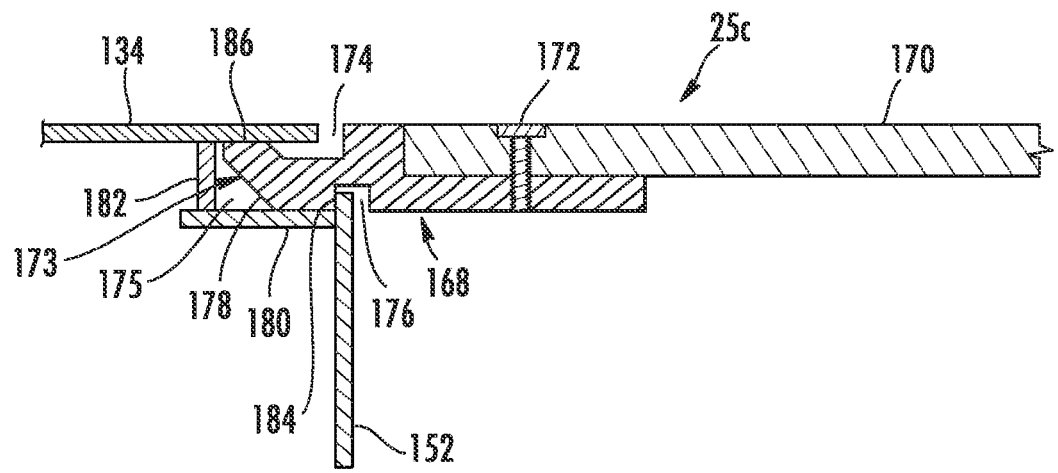
FIG. 6 is a detail of the equine table, showing a cantilever for supporting an appendage of a horse.

Referring to FIG. 6, the cantilevers 25a-25d (see also FIGS. 1 and 2) have a bracket portion 168 and an extension portion 170 affixed together by a mechanical fastener 172 or other conventionally known means. By being of a two piece construction, extension portions of different shapes and sizes may interchangeable but used with a particular bracket portion 168. Notwithstanding, it is to be understood that other constructions for the cantilevers, such as being of a one-piece construction, are also within the scope of this invention. The cantilevers 25a-25d are preferably made of a radiolucent material, such as for example carbon fiber.

The bracket portion 168 includes a tongue 173 that is received within an annular channel 175 defined by the top plate 134 (including walls 180, 182 and the skirt 152). The tongue 173 and channel 175 communicate to removeably secure the cantilevers 25a-25d (FIGS. 1 and 2) in position for supporting horse appendages (e.g., head, legs and rump). In the preferred embodiment, the tongue 173 is provided with first and second slots 174, 176 and a beveled proximal end 178 to assist placing the tongue 173 within the annular channel 175. An upper end 184 of the skirt 152 and the underside 186 of the top plate 134 restrict movement of the tongue 173 from inadvertent removal from the channel 175. The cantilever (e.g. cantilever 25c; see also 25a-b and d of FIGS. 1 and 2) maintains its position with the top plate 134 due to weight of the cantilever 25c and any part of the horse lying thereon. That is, weight on the distal portion of the cantilever 25c causes the cantilever 25c to become secured by engaging the top plate 134 within the channel 175. To move the cantilever 25c to a new location around the annular channel 175, or remove the cantilever 25c, weight is offset from the distal end by an operator such that the cantilever 25c may be slid to a new location or removed. In this manner, communication between the tongue 173 and annular channel 175 allows for the cantilever 25c may be moved infinitely to any location around the perimeter of the carousel 26. Although only one of the cantilevers 25c was illustrated in detail, it is to be understood that each of the cantilevers 25a-25d function the same way. Moreover, other items, such as an I.V. (not shown) could be attached to a cantilever in order to allow for removal and relocation of the I.V.

Referring to FIGS. 1 and 2, the electrical control unit 78 provides for operation of the aforementioned electrical components of the table 10. Programming and interaction with the electrical controls unit 78 is provided by a control panel 190. Optionally, batteries may be provided as a back-up energy source in order to present an emergency retreat option should the electrical power supply be interrupted.

In use, the cantilevers 25a-d are moved about the carousel 26 to a proper position dependent on the animal and body part to be examined. A hoist is used to place a horse on the equine table 10. If necessary, the height adjustment system 46 is utilized to lower the table 10 by removing air from the air springs 48 in order to ease loading of the horse on the table 10. The table 10 is then raised, by inflating the air springs 48, to a height that allows for the table 10 to be positioned over the patient couch 18. The table 10 is manually moved via handles 196 to the docking system 145 whereat v-notched castors 84b ride on the complementary rail 96. The table 10 is pushed forward on the rail 96 until reaching a predetermined stop 98. In this manner the table 10 is quickly, consistently and accurately positioning in relation to the CT system 12. The cantilevers 25a-d may be manually adjusted as necessary to properly position the appendages of the animal. And, the operator may linearly and radially move the horse by manually pushing the top plate 134 of the carousel 26 in the desired direction. As the couch 18 moves during the examination, the motion tracking and actuating system 27, 28 cause the carriage 100 to mimic the movement of the couch 18 into and out of the gantry 14.

Referring to FIGS. 12-25, an alternative embodiment of the invented equine table 10a is illustrated. Elements in the various embodiments with same reference number indicate that the element is the same or substantially similar to each other in each of the embodiments. The equine table 10a is as described herein with respect to that described in reference to FIGS. 1-11, and the above description of all elements are incorporated into the embodiment illustrated by FIGS. 12-15, except for that disclosed herein as it relates to a carousel 26a, wherein the carousel 26a has a different configuration and components for allowing movement of the carousel 26a and locking it into a desired position, as compared to the carousel 26 with template 130, ball bearings 140 and pneumatic locks 154 of the embodiment described in reference to FIGS. 1-11. In particular, linear bearing assemblies 107b are utilized for positioning (left/right) of the top plate 134. The linear bearing assemblies 107b in combination with linear bearing assemblies 107a allow for the top plate 134 and thus patient to be moved in a horizontal x-z plane (left/right/forward/back/diagonally), and roller assemblies 200, 202 allow for rotational movement of the top plate 134 and thus patient to any angle radially about a vertical axis Y (yaw) of the table 10a. Angular and linear movement of the top plate 134 is independent of the remaining portions of the table 10a whereby the top plate 134 and patient thereon may be selectively moved forward, rearward, left or right, or at any angle there-between, or radially, with respect to remaining table components (e.g. the frame 23, legs 24, actuating systems 28, base plate 132a, etc.), docking system 145 (FIG. 2) and CT system 12 (e.g. the gantry 14 and couch 18).

In FIGS. 12-25, portions have been cut-away, details simplified, and elements omitted in the various views to improve clarity of the drawings. For example, some elements of FIG. 12 are omitted from FIGS. 13 and 15. Nevertheless, it is to be understood that the Figures are to be considered collectively and thereby elements shown in a Figure are necessarily in other Figures. For example, it is clear to one skilled in the relevant art in viewing FIG. 12, that elements shown on the left side of FIG. 13 of the carousel 26a necessarily have equivalent elements located on the right side of the carousel 26a even though such elements are not shown there.

The carousel 26a of the alternative embodiment includes a base plate 132a and a top plate 134 (uppermost plate). Linear bearing assemblies 107b provided on the carriage 100 allow for the carousel 26a to move in a transverse, linear direction, preferably but without limitation about 3 inches left and right of a center for positioning of the patient. The bearing assemblies 107b include bearings 108b which ride rails 106b undermounted on the base plate 132a.

The carriage 100 carries transverse lock assemblies 212 for selectively disallowing transverse linear movement of the base plate 132a otherwise permitted by the bearing assemblies 107b. To effectuate the bearing lock assemblies 212, a pneumatic cylinder 214 drives a pad 216 upward into engagement with the base plate 132a.

The base plate 132a includes inner and outer rings of roller assemblies 200, 202 to allow 360 degree rotation of the top plate 134. The roller assemblies 200, 202 includes shafts 201, 203 and respective rollers 204, 206 which engage, support and permit rotation of the top plate 134 which sits atop of the rollers 204, 206, thereby allowing controlled rotational positioning of the patient. The roller assemblies 200, 202 are attached to the base plate 132a by brackets.

The base plate 132a carries rotational lock assemblies 218 for selectively disallowing rotational movement of the top plate 134 otherwise permitted by the roller assemblies 200, 202. To effectuate the rotational lock assemblies 218, a pneumatic cylinder 220 drives a pad 222 upward into engagement with the top plate 134.

The base plate 132a also is provided with a plurality of centering bearing assemblies 208, e.g. four bearing assemblies 208, which include bearings 210 which engage a perimeter wall of the top plate 134. Brackets 135 are provided to attach the bearing assemblies 208 to the base plate 132a.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed is:

1. A radiation system for the examination and/or treatment of large patients, comprising: a table capable of carrying a large patient, said table including: a frame positionable over a couch; a carousel carried by said frame and configured for placement of the large patient thereon; a motion tracking system carried by said frame wherein said motion tracking system detects movement of said couch and transmits signals to an actuating system when said couch moves; wherein said actuating systems causes said carousel to move when said couch moves; linear bearing assemblies capable of allowing movement of the patient in a horizontal plane leftwards and rightwards relative to the couch; and roller assemblies capable of allowing movement of the patient radially relative to a vertical axis.

2. The radiation system according to claim 1, wherein said motion tracking system synchronizes movement of said carriage with that of said couch.

3. The radiation system according to claim 1, wherein said motion tracking system includes a magnet that moves with and is carried by said couch and a transducer that communicates with said magnet as said couch moves in order to produce said signals.

4. The radiation system according to claim 1, wherein said motion tracking system includes a laser directed at said couch to detect movement of said couch and a transducer that communicates with said laser as said couch moves in order to produce said signals.

5. The radiation system according to claim 1, wherein said actuating system includes a motor to drive said carousel and at least one track attached to said frame, wherein said carousel travels on said at least one track when being driven by said motor.

6. The radiation system according to claim 1, further including at least one cantilever attached to said carousel for carrying an appendage of the large patient.

7. The radiation system according to claim 6, wherein said at least one cantilever is infinitely positionable around the perimeter of said carousel.

8. The radiation system according to claim 1, wherein said carousel is manually moveable radially and linearly relative to said frame.

9. The radiation system according to claim 1, further including a docking system having a rail, a castor mounted to said frame, wherein said caster includes a notch which communicates with the rail for positioning of said table to said couch.

10. The radiation system according to claim 1, wherein said carousel includes a top plate and said top plate is manually movable radially and linearly relative to said frame.

* * * * *